(12) United States Patent
Pison et al.

(10) Patent No.: US 8,846,580 B2
(45) Date of Patent: Sep. 30, 2014

(54) DIAGNOSTIC NANOSENSOR AND ITS USE IN MEDICINE

(75) Inventors: Ulrich Pison, Berlin (DE); Michael Giersig, Berlin (DE); Alex Schaefer, Berlin (DE)

(73) Assignee: Gilupi GmbH, Berlin (DE)

( * ) Notice: Subject to any disclaimer, the term of this patent is extended or adjusted under 35 U.S.C. 154(b) by 1325 days.

(21) Appl. No.: 11/917,032

(22) PCT Filed: Jun. 9, 2006

(86) PCT No.: PCT/EP2006/005760
§ 371 (c)(1),
(2), (4) Date: Jan. 20, 2009

(87) PCT Pub. No.: WO2006/131400
PCT Pub. Date: Dec. 14, 2006

(65) Prior Publication Data
US 2009/0131274 A1    May 21, 2009

Related U.S. Application Data

(60) Provisional application No. 60/744,652, filed on Apr. 11, 2006.

(30) Foreign Application Priority Data

Jun. 10, 2005  (EP) .................................... 05090170
Jan. 19, 2006  (EP) .................................... 06090012

(51) Int. Cl.
| | | |
|---|---|---|
| *G01N 33/543* | (2006.01) | |
| *B82Y 30/00* | (2011.01) | |
| *G01N 21/64* | (2006.01) | |
| *B82Y 5/00* | (2011.01) | |
| *B82Y 25/00* | (2011.01) | |
| *G01N 21/55* | (2014.01) | |
| *B82Y 15/00* | (2011.01) | |
| *G01N 21/25* | (2006.01) | |

(52) U.S. Cl.
CPC .......... *G01N 33/54373* (2013.01); *B82Y 30/00* (2013.01); *G01N 21/6489* (2013.01); *B82Y 5/00* (2013.01); *B82Y 25/00* (2013.01); *G01N 21/554* (2013.01); *G01N 2021/258* (2013.01); *B82Y 15/00* (2013.01); *Y10S 977/882* (2013.01); *Y10S 977/891* (2013.01)
USPC .................. 506/32; 435/4; 977/882; 977/891

(58) Field of Classification Search
USPC .......................... 435/4; 506/32; 977/882, 891
See application file for complete search history.

(56) References Cited

U.S. PATENT DOCUMENTS

| | | |
|---|---|---|
| 2004/0005723 A1 | 1/2004 | Empedocles et al. |
| 2004/0180379 A1* | 9/2004 | Van Duyne et al. ........... 435/7.1 |
| 2007/0115474 A1 | 5/2007 | Chaton et al. |
| 2008/0213130 A1 | 9/2008 | Pison et al. |
| 2009/0131274 A1 | 5/2009 | Pison et al. |

FOREIGN PATENT DOCUMENTS

| | | |
|---|---|---|
| WO | 2004/003535 A1 | 1/2004 |
| WO | 2004/086044 A1 | 10/2004 |
| WO | 2005/031299 A2 | 4/2005 |
| WO | 2005/033335 A2 | 4/2005 |
| WO | 2005/059952 A2 | 6/2005 |
| WO | 2005/114298 A2 | 12/2005 |

OTHER PUBLICATIONS

C. Vericat et al., Thiol-Capped Gold: From Planar to Irregular Surfaces, 20 J. Phys.: Condens. Matter 184004 (2008).*
A. Kosiorek et al., Fabrication of Nanoscale Rings, Dots, and Rods by Combining Shadow Nanosphere Lithography and Annealed Polystyrene Nanosphere Masks, 1 Small 439-444 (2005).*
I.-S Park and N. Kim, Thiolated Salmonella Antibody Immobilization Onto the Gold Surface of Piezoelectric Quartz Crystal, 13 Biosens. Bioelectron. 1091-1097 (1998).*
G. Raschke et al., Biomolecular Recognition Based on Single Gold Nanoparticle Light Scattering, 7 Nano Lett. 935-938 (2003).*

* cited by examiner

*Primary Examiner* — Randy Boyer
(74) *Attorney, Agent, or Firm* — Buchanan Ingersoll & Rooney PC (57) ABSTRACT

This invention relates generally to biosensor technology, and pertains more particularly to novel multifunctional biosensors based on ordered arrays of metallic, semiconductors and magnetic nano-islands for medical, biological, biochemical, chemical and environmental applications.

20 Claims, 12 Drawing Sheets

DIAGNOSTIC NANOSENSOR AND ITS USE IN MEDICINE

FIELD OF THE INVENTION

This invention relates generally to biosensor technology, and pertains more particularly to novel multifunctional biosensors based on ordered arrays of metallic, semiconductors and magnetic nano-islands for medical, biological, biochemical, chemical and environmental applications.

BACKGROUND OF THE INVENTION

The nanoscale science and engineering have shown great promise for the fabrication of novel biosensors with faster response and higher sensitivity than that of planar sensor configurations, due to their small dimensions combined with a dramatically increased contact surface and strong binding with biological and chemical reagents. Such biosensors have important applications in medicine, in biological and biochemical research, as well as for environmental monitoring and protection and in food industry.

In the last few years nanoparticle technology has been used to build chemical sensors and biosensors for detecting various analytes from contaminants in air to the presence of particular DNA segments in blood and other samples.

Encapsulated metal nanoparticles could be functionalized with different kind of ligands to give a chemical sensor that uses changes in the electrical characteristics of the metal nanoparticle and thus could function as an electronic nose for gas phase or electronic tongue for liquid phase as described for example in the US 2005/0142030.

In addition the WO 2004/086044 discloses that silver nanoparticles or gold nanoparticles could serve as nanosensors in one or the other way if appropriately sized and functionalized. However, to take full advantage of the physical characteristics of small sized particles such as for localized surface plasmon resonance (LSPR) spectroscopy as detection method, these particles need to have even size and physical characteristics and/or need to be even geometrically organized on substrates.

Another limitation of metal nanoparticles as described in the above mentioned documents is their production via wet chemical synthesis. This type of production disables the precise control on size and shape of the particle and does not permit even immobilization of particles on substrates.

More recently, chemical and biosensors utilizing nanotubes such as single- or multi-walled carbon nanotubes have been proposed. Such sensors were produced using conventional semicconductor fabrication techniques to give non-horizontal or horizontal orientated nanotubes or -wires on solid surfaces as described in WO 2005/031299 or in WO 2005/093831. However, conventional semicconductor fabrication techniques do not allow the geometric organization of nanostructures on solid surfaces as lithographic techniques do.

Lithography as technique for the production of nanostructured surfaces exist in various types. One type of lithography is electron beam lithography and has been used for example in FR 2 860 872 to create a distribution of circular or ellipsoidal "plots" on a two dimensional surface, or to it. A grat disadvantage of this technique is that it is very cost-intensive.

Electrodeposition of nanoparticles on nanotubes or wires as described in US 2005/0157445 gives miniaturized electrical devices but need conductive elements.

SUMMARY OF THE INVENTION

It is the primary objective of this invention to address the novel multifunctional biosensor technology based on metallic semiconductors and magnetic nanoislands and nanoisland arrays giving a new nanosensor for diagnostic purposes in medicine, biological and biochemical research, as well as in environmental monitoring and protection and in food industry. The surface of nanoparticles can be functionalized with bio-organic interactive material that due to their specificity interact selectively with other molecules. By chemically controlling the surface of the nanoparticles, they can be "programmed" to recognize and selectively bind molecules, other nanoparticles (semiconductors) or a suitably patterned substrate surface like the cellular outer membrane.

Particularly, it is an objective of this invention to provide nano-transducers based on noble metal nanoislands through resonant excitations of the collective oscillations of the conduction electrons on the nanoislands, the so-called surface plasmon resonances. This phenomenon can be coupled to the binding event between receptors and their targets. Highly improved electrical conductivity of these nano-transducers translate into unprecedented sensitivity and enable the design of novel sensing devices for the detection of pathogens and toxins of concern, to homeland security, food safety, environmental quality, and public health.

The use of noble metallic nanoislands results in increased signal transduction of the binding event between bio-organic interactive material and their target substances and lead to an increase in sensitivity of the nano-biosensor in terms of lower limit and dynamic range of detection.

The present invention overcomes the following limitations of prior art:

High production cost such as in electron beam lithography and in electrodeposition;

Uneven distribution/immobilisation of nanoparticles, -tubes or -wires on substrates as in conventional semicconductor fabrication techniques;

Uneven size and shape of particles due to wet chemical synthesis.

The present invention provides surface-confined noble-metallic nanotriangles that are distributed in hexagonal geometry, and the dimension of this hexagonal geometry can be varied by means of nanosphere lithography (NSL).

Besides surface-confined nanotriangles, surface-confined nanospheres and rod-shaped horizontal nano-morphologies can be obtained from the nanotriangles via an additional sintering process. The signal transduction mechanism of the diagnostic nanosensor according to the invention is based on its sensitivity to local refractive index changes as a function of periodic, size- and shape-controlled, surface-confined noble-metallic nanostructures. The nanosensor according to the invention due to periodic distribution is demonstrated to be sufficiently sensitive for the detection of ultra-low levels of biomarkers in physiological fluids. Further, the nanosensor shows minimal nonspecific interactions after bioconjugation, and allows for the analysis of biological species in a surfactant-free environment. This is extremely important because the absence of a surfactant allows for biological species to be analysed in their native state.

DESCRIPTION OF THE INVENTION

A highly periodic array of metallic nanoislands acting as nanotranducers forms a new integral structure called a "Diagnostic-Nanosensor". This "Diagnostic-Nanosensor" is deposited on a device that could have a form like a needle or wire or tube or chip and made out of transparent (glass, sapphire) or non-transparent material (silicon substrates, stainless steel, biocompatible polymers). The "Diagnostic-Nanosensor" is made by using nanosphere lithography (NSL)

to create metallic nanoislands. This technique allows the total control of size and shape of the functional part of the nanosensor.

One important feature in the optical spectra of nanoislands or nanosized metal particles (Ag, silver; Au, gold) is the surface plasmon band. The surface plasmon band is due to collective electron oscillation around the surface mode of the particles. For example Ag nanoparticles have a strong absorption around 390 nm while Au nanoparticles have the plasmon band around 520 nm. The peak position and bandwidth of the surface plasmon absorption are related to the size and shape. For gold nanorods, however the absorption spectrum changes dramatically and a bimodal spectrum can be detected with peak position dependent on the aspect ratio of the nanorods.

Figure 10:
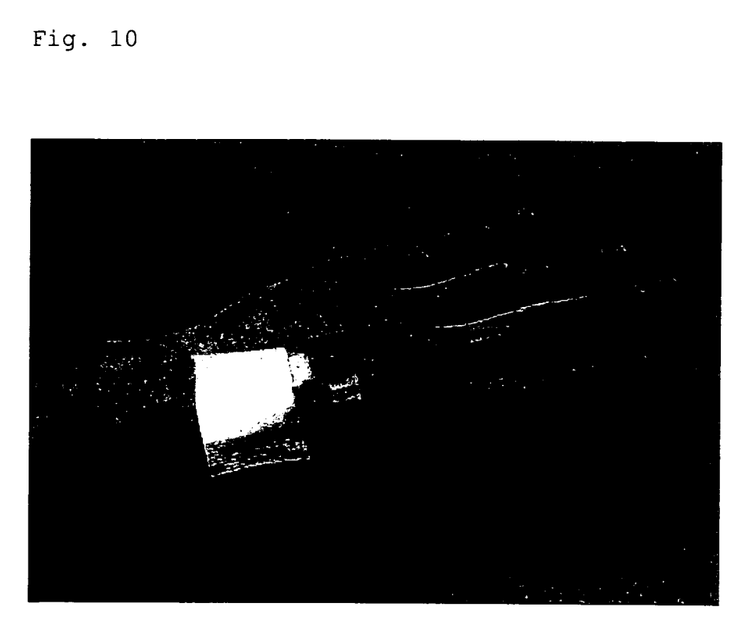
FIG. 10: Cell select catheter in place. A spring wire with diagnostic nanosensors assembled on its surface is put into a peripheral vein through a standard venous line. After appropriate incubation time the cell select catheter is replaced with rare molecules or cells of interest attached to its surface for further laboratory analyses.

The subsequent modification of nanostructured surfaces of a catheter or spring wire with bio-organic interactive material is presented as an example in FIG. 10. This step and especially the binding of DNA, other molecules or cells on the particles surfaces leads to a change in the dielectric constant of this system and can easily be detected by the optical method. The Diagnostic Nanosensor achieves nanometer scale spatial resolution and therefore provides accurate real-time information regarding not only the concentration of a specific analyte of organic or inorganic nature but also its spatial distribution. The operation of sensors made with nanowires, nanotubes, or nano-contacts is based mostly on the reversible change in the optical and electronic properties In general the sensitivity and specification of the Diagnostic-Nanosensor according to the invention is based on quantum size effect and can be occur with the decreasing the size of nanoparticles according to the invention.

The "Diagnostic-Nanosensor" of this invention may be used to detect biological materials, such as proteins, carbohydrates, or nucleic acids or cells as well as non-biological materials, such as synthetic polymers or non organic nanoparticles. The "Diagnostic-Nanosensor" could be used under in vivo as well as in vitro conditions.

The present invention takes into account the funktionalization the surface-confined noble-metallic nanostructures with long chain heterobifunctional cross-linkers. The cross-linkers enable a stable bioconjugation of the surface-confined noble-metallic nanostructures with specific antibodies.

The nanosensor due to its periodic distribution is demonstrated to be sufficiently sensitive for the detection of ultralow levels of biomarkers in physiological fluids. Further, the nanosensor shows minimal nonspecific interactions after bioconjugation, and allows for the analysis of biological species in a surfactant-free environment. This is extremely important because the absence of a surfactant allows for biological species to be analysed in their native state. These three important aspects of the present inventions are not known from the state of the art like.

ADVANTAGES OF THE INVENTION

In the biomedical and human area there is a need for better detection and diagnosis. The nanoscale materials are insatiable for producing new detection and diagnostic devices. On the nanometer length scale, materials exhibit new properties such quantum size confinement. Their surface properties become increasingly important. Nanoparticles made of metals (gold, silver, etc), semiconductors (CdS, CdTe, CdSe, Si, etc) or (superpara-) magnetic particles form an ideal platform for functionalized nanoscale materials. The particles size can be varied from some of nanometer to 100 nm. The small particle size implies high sensitivity and selectivity if they could further functionalized by the precise deposition of bio-organic interactive material for the binding of a given analyte.

The "Diagnostic-Nanosensor" according to the invention is made by using nanosphere lithography (NSL) to create metallic nanoislands. This technique allows the total control of size and shape of the functional part of the nanosensor down to sizes below 10 nm. Subsequent depositions of bio-organic interactive material on the nanostructures give a sandwich device for interacting with organic or inorganic targets. Because the sensitivity and specification of any biosensor depends on the size of a given sensor unit, the invention descript here allows sensitivities far below the pmol range. In general, the Diagnostic-Nanosensor according to the invention is based on quantum size effect and can be tuned with decreasing the size of utilized nanoparticles that are deposited on various support materials and are subsequently functionalized with bio-organic interactive material to give a sandwich device for interacting with organic or inorganic targets.

Assembling the "Diagnostic Nanosensor" on biocompatible supports like spring wire or catheter material as used in medicine the "Diagnostic Nanosensor" gives a molecular/cell select catheter that could be applied for in vivo diagnostic purposes. As such the "Diagnostic Nanosensor" according to the invention is for the direct detection and isolation of rare molecules or cells out of the peripheral blood or the body. This application technique enables diagnostic procedures that were not possible before: prenatal diagnoses of chromosomal aberration using foetal trophoblasts present in maternal circulation; cancer diagnoses and monitoring of cancer therapy based on the detection of disseminated cancer cells in the body.

The "Diagnostic Nanosensor" according to the invention allows detection of a resultant interaction between the bio-organic interactive material and the target substance by measuring the collective oscillations of the conduction electrons on the nanoislands, the so called surface plasmon resonance, or detection of optical properties from semiconductors particles (luminescence), or the super-paramagnetic properties by magnetic particles. These detection methods enable the use of the "Diagnostic Nanosensor" according to the invention on scene, i.e. without the infrastructure of a laboratory. Thus, the "Diagnostic Nanosensor" could be used at the bedside, in the operating theatre, in the ambulance, and on battle field.

The surface treatment of Nanosensors with NSC leads to surprising results:
  departure from the beaten track
  a new perception of the problem
  satisfaction of a long-felt need or want
  hitherto all efforts of experts were in vain
  the simplicity of a solution proves inventive action, especially if it replaces a more complex doctrine
  the development of scientific technology moved in another direction
  the achievement forwards the development
  misconceptions about the solution of the according problem (prejudice)
  technical progress, such as: improvement, increased performance, price-reduction, saving of time, material, work steps, costs or resources that are difficult to obtain, improved reliability, remedy of defects, improved quality, no maintenance, increased efficiency, better yield, augmentation of technical possibilities, provision of another (not necessarily better) product, opening of a second (not necessarily better) way, opening of a new field, first solution for a task, spare product, alternatives, possibility of rationalisation, automation or miniaturisation or enrichment of the pharmaceutical fund special choice (if a certain possibility, the result of which was unforeseeable, is chosen among a great number of possibilities, that is a patentable lucky choice)

error in a citation young field of technology combined invention; a combination of a number of known elements, with a surprising effect licensing praise of experts and commercial success The method for producing the diagnostic-nanosensor comprises two separate but interrelated procedures:

(1) The production of periodic arrays of nanostructures.

(2) Functionalizing nanostructured arrays using bio-organic interactive material that could be bound to the arrays directly or indirectly through linker technologies.

(1)

Figure 1:
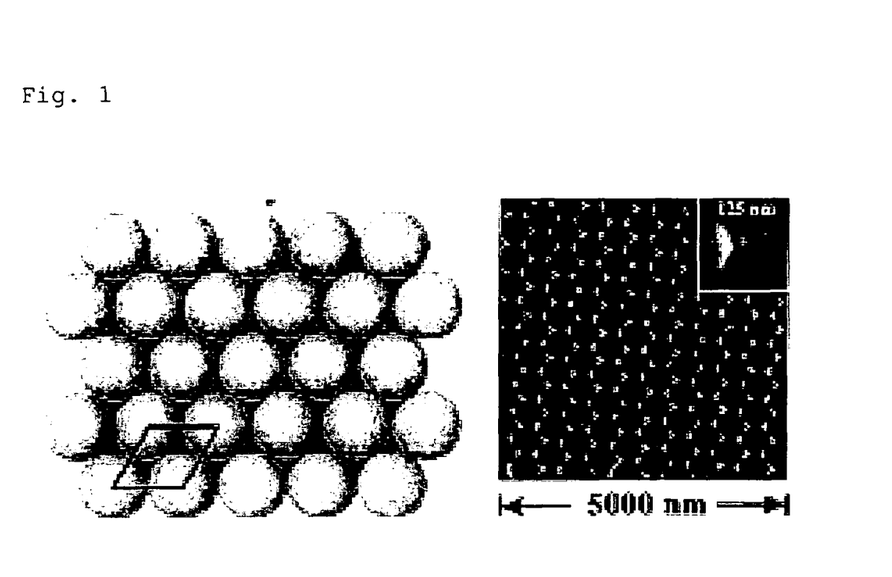
FIG. 1: Schematic illustration (a) and typical AFM image (b) of gold nanoparticles after evaporation process and liftoff of the mask

To produce periodic arrays of nanostructures, a relatively inexpensive and simple method of nanoparticles or nanospheres lithography (NSL) will be used for the creation of periodic and quasi-periodic self assembly spherical objects like polystyrene or silica particles with a diameter in the range of 200 to 2000 nm (FIG. 1a). The two and three-dimensional (2-D, 3-D) ordered particles will be used as a mask for the following deposition of various amounts of different metals (Au, Ag, Pt) or semiconductors (CdS, CdTe, CdSe). After the evaporation process the liftoff of the mask will be performed. The metallic 2-D (FIG. 1b) or 3-D varying particle arrays permit the control of the distance between the nanoparticles as well as their cubic, hexagonal or more complicated ordering. The amount of the deposited materials through the mask can determine directly their optical and electronic properties.

The production of periodic arrays of nanostructures involves the following steps:

a) Production of a two dimensional mask that consists of spherical monodisperse polystyrene particles of sizes from 200 nm to 7000 nm. This production involves the controlled aggregation of the particles between solvents of different surface behaviour for the precise structuring of the two dimensional mask. The final morphology of the mask is determined using temperature and mechanical treatment to give triangles, roots, dots or others.

b) Deposition of the mask on planar substrates (plates or chip) or non-planar substrates (catheters, spring wires, stents). The substrates could be biocompatible for in vivo applications of the sensor.

c) Evaporation of noble metals, semiconductors or magnetic materials (gold, platinum, silver, CdSe, CdTe, Cobalt, Nickel) through the mask.

d) Dissolving the mask by temperature or chemical treatment.

(2)

Figure 7:
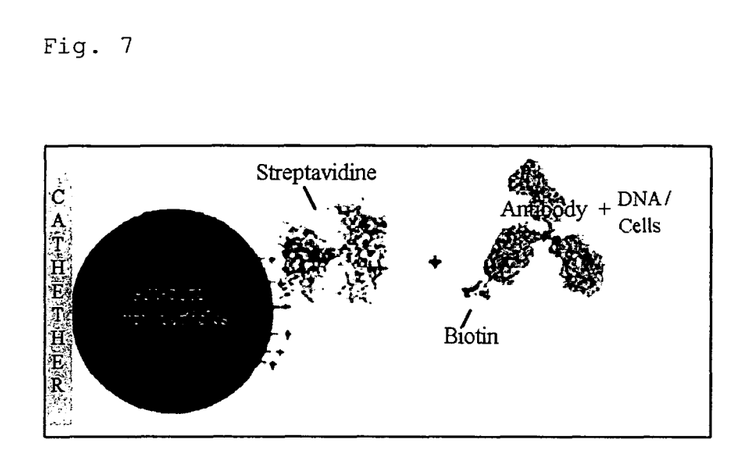
FIG. 7: Graphic presentation of how DNA or cellular structures are detected by specific antibodies. Antibodies are cross linked through streptavidin-biotin to Au-nanoparticles. Au-nanoparticles decorate the nanostructured surface of a catheter or spring wire or stent. This technique is the first nanosandwich approach for the production of a Diagnostic Nanosensor.

To functionalize nanostructured arrays, bio-organic interactive material is bound to array surfaces using various strategies. These strategies include standard streptavidin-biotin interaction as shown in FIG. 7. It also includes the direct binding of (monoclonal) antibodies like IgG or fragments there of to the array surface via adhesion or electrostatic interaction. In addition, covalent linkage of target-specific molecular structures like antibodies or fragments there of, oligomers made of nucleic acids, or peptide or glycopeptides could be performed using linker technology as described in the detailed example below. The latter technique allows the precise binding of target specific molecules to nanoislands giving nanometer scale spatial resolution and therefore provides accurate real-time information regarding not only the concentration of a specific analyte but also its spatial distribution.

The "Diagnostic-Nanosensor" is for medical application, for biological and biochemical research, as well as for environmental monitoring and protection and food safety. Concerning medical application, the "Diagnostic-Nanosensor" is assembled as a device for (1) in vivo and (2) in vitro use.

(1): The "Diagnostic-Nanosensor" for In Vivo Use

Figure 9:
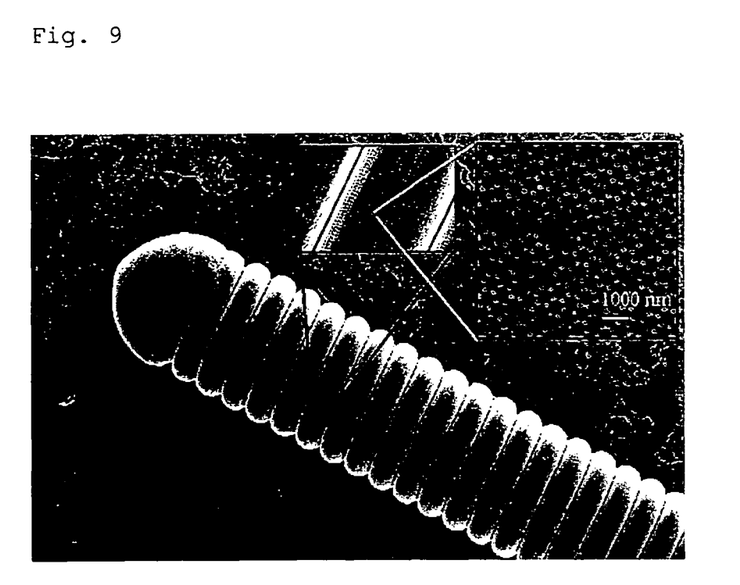
FIG. 9: Diagnostic nanosensors assembled on spring wire to give a cell or molecular select catheter.

For the in vivo device the "Diagnostic Nanosensor" is assembled on spring wire giving a molecular or cell select catheter to obtain rare molecular or cellular components directly out of the circulation or the body in general (FIG. 9).

As device for in vivo appliance the "Diagnostic-Nanosensor" assembled on e.g. spring wires gives a cell or molecular select catheter which is useful for prenatal diagnosis of chromosomal aberrations, cancer diagnosis and the monitoring of chronic diseases like cancer, metabolic, infectious, allergic and inflammatory diseases. This device is applied as descript below.

a) Puncture of a blood vessel (vein or artery) using a hollow needle.

b) Putting the nanosensor through the hollow needle or through a standard venous line into the blood vessel as shown in FIG. 9.

c) Replacing the needle but keeping the nanosensor in place.

d) After the appropriate incubation time (between 5 to 60 minutes) the nanosensor is replaced with the attached cells and/or molecules for further processing.

As a cell select catheter the "Diagnostic Nanosensor" according to the invention is for the isolation of rare cells out of the peripheral blood, e.g. trophoblasts. Trophoblasts are foetal cells that appear in maternal blood around the $7^{th}$ gestational week at a concentration of about 1-2 per ml. The cell select catheter equipped with a monoclonal antibody that is directed against cellular but not soluble HLA-G binds specifically circulating trophoblasts in maternal blood. The number of bound cells to the cell select catheter depends on the retention period in the maternal circulation and the actual cell concentration. Appropriate numbers of trophoblasts for prenatal diagnoses of chromosomal aberration and other genetic defects could be collected after a retention period of 30±15 minutes in vivo. After replacing of the catheter the tip of the catheter with the attached cells is placed into a collector tube for transport to specialized laboratories.

(2) The "Diagnostic-Nanosensor" for In Vitro Use

For the in vitro device the "Diagnostic Nanosensor" is assembled on planar and transparent support to give a "lab on a chip" allowing quantitative and qualitative determination of targets by measuring the plasmon resonance frequencies on the nanostructured surfaces or luminescence or magnetic properties depending on the material that is deposited onto the support using nanosphere lithography.

As device for in vitro appliance the "Diagnostic-Nanosensor" is for "on scene" diagnostic procedures (e.g. at the bedside, in the operating theatre, the ambulance, or the battle field) that should be used as described below.

Figure 11:
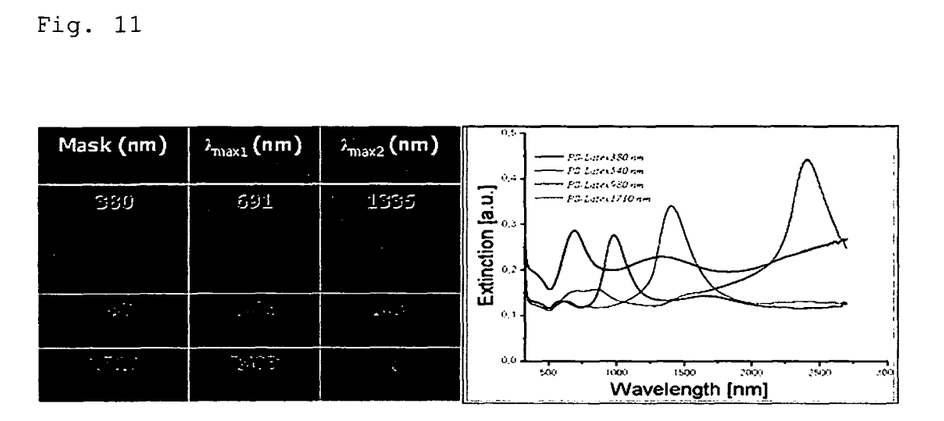
FIG. 11: Influence of particle size on plasmon resonance. Different size of the mask (380, 540, 980, or 1710 nm) gives correspondent nanoparticle depositions on transparent substrate that generate typical spectra.

According to the quantum size confinement effect nanosized metallic particles show different optical absorption spectra depending on size. The surface plasmon band is due to collective electron oscillation around the surface of the particles. For example Ag (Silver) nanoparticles have plasmon band around 390 nm while Au nanoparticles have the plasmon band around 520 nm. The pick position, intensity and bandwidth of the surface plasmon absorption are directly related to size, morphology (shape), and surface functionality of the particles (see FIGS. 11 & 12).

Figure 12:
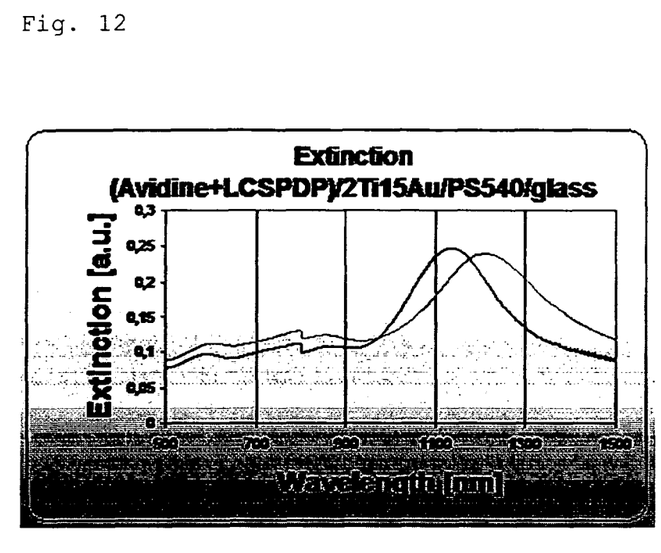
FIG. 12: Typical example of spectrum changes of the plasmon resonance after deposition of bio-interactive material (avidin in this case) on nanostructured arrays.

By covering the 2-dimensional assemblies of gold nanoparticles with avidin their plasmon peak shifts toward longer wavelength and can be easily detected as shown in FIG. 12.

The invention may be further illustrated by the following examples:

EXAMPLE 1

The two-dimensional ordering of latex particles as a basis for nanosphere lithography (NSL) has been used by us and others in the past [1,2,3,4,5,6,7,8]. The evaporation or sputtering of different materials through a latex particle mask enabled the production of lattices of triangular islands on various substrates, the shape of the islands being determined by the shape of the aperture between the spheres in the mask. Clearly, the size of the aperture between the spheres depends on the size of the beads in the monolayer. To overcome this limitation, we annealed the monolayer to downsize the apertures in the mask from an initial 200 nm to 30 nm. This result was far beyond our expectations, and was essential for the fabrication of nanodot particles (FIG. 6) and isolated nanorings (FIG. 7).

[1] H. W. Deckman, J. H. Dunsmir, Appl. Phys. Lett. 1982, 41, 377.
[2] M. Giersig, P. Mulvaney, Langmuir 1993, 9, 3408.
[3] H. W. Deckman, J. H. Dunsmuir, Appl. Phys. Lett. 1982, 4, 377.
[4] J. C. Hulteen, R. P. Van Duyne, J. Vac. Sci. Technol. A 1995, 13, 1553.
[5] M. Winzer, M. Kleiber, N. Dix, R. Wiesendanger, Appl. Phys. A 1996, 63, 617.
[6] R. Micheletto, H. Fukuda, M. Ohtsu, Langmuir 1995, 11, 3333.
[7] F. Burmeister, W. Badowsky, T. Braun, S. Wieprich, J. Boneberg, P. Leiderer, Appl. Surf. Sci. 1999, 461, 144.
[8] N. D. Denkov, O. D. Velev, P. A. Kralchevsky, I. B. Ivanov, H. Yoshimura, K. Nagayama, Langmuir 1992, 8, 3183.

In our recent work we demonstrated that if the sample is moving during the deposition process, the evaporated structures can become much more complex and range from cup-like structures to rods and wires.[9] Now, we improved our technique further. Improvements involve decreasing the size of the apertures between particles by temperature treatment applied to the nanosphere mask before the evaporation process, and using different material in nanometer size for the deposition on various supports.

[9] A. Kosiorek, W. Kandulski, P. Chudzinski, K. Kempa, M. Giersig, Nano Lett. 2004, 4, 1359.

1. Nanosphere Mask Preparation

A piece of silicon, stainless steal, glass or sapphire substrate (1 cm$^2$) could be used for the deposition of polystyrene (PS) latex particles. In this first step, the latex particles (diameter=540 nm) in ethanol/water solution are slowly applied to the surface of water in a 15 cm Petri dish using a glass pipette. The amount of solution that could be distributed to cover the whole water surface with a hexagonal close packed (hcp) monolayer is limited by the size of the Petri dish and the diameter of the spheres. About 70% of this amount of solution is applied to the surface of the water, which left some places for stress relaxation and avoided the formation of cracks in the lattice during the next steps of the preparation. At this stage the monolayer has the biggest crystals of about 2 cm$^2$, with very irregular shapes. To promote the growth of large crystals, gentle waves are applied to the liquid medium by slow and careful vessel tilting. After this treatment, crystals of about 25 cm$^2$ are created that show clear diffraction colors. Finally, the monolayer is deposited on a substrate by slow water evaporation.

2. Annealing

Figure 2:
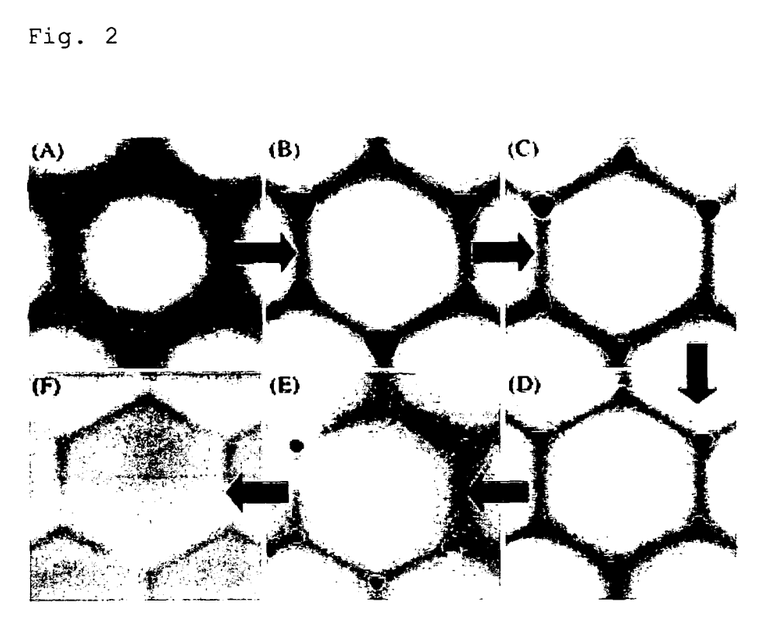
FIG. 2: A 540-nm PS latex mask annealed in 25 mL of water/EtOH/acetone mixture by A) 1, B) 2, C) 4, D) 6, E) 7, and F) 10 microwave pulses.
Figure 3:
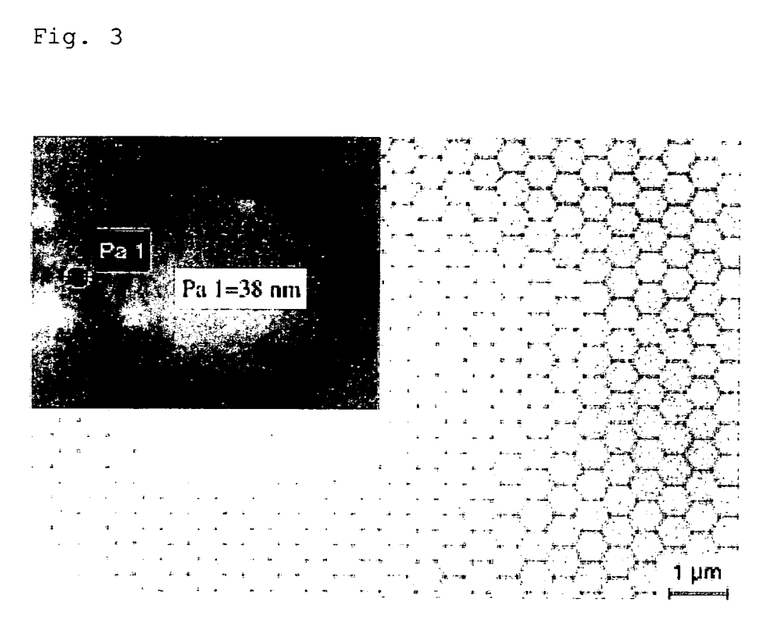
FIG. 3: SEM image of the annealed 540-nm PS latex mask with sizes of all apertures below 50 nm.

After the drying process, annealing of masks is performed. The monolayer of 540-nm PS latex nanospheres on a conductive Si substrate is immersed in a mixture (25 mL) of water/ethanol/acetone (3:1:1). Microwave heating is used up to the boiling temperature of the mixture, then additional microwave pulses are applied with duration of 3 s and period of 28 s. The increasing number of pulses causes gradual mask annealing and a decrease of the size of the apertures. The dependence of aperture morphology on number of pulses is presented in FIG. 2. The liquid environment of the sample ensured very homogeneous annealing—the feature sizes become uniform over the whole area of the sample. The control of the aperture size was very good and reproducible. With the 540-nm PS latex monolayer we were able to adjust the aperture size from an initial 200 nm to 25 nm (FIGS. 2 and 3). The annealed masks have different thicknesses—the more the sample is annealed, the flatter and thinner it is.

3. Metal Deposition

Figure 4:
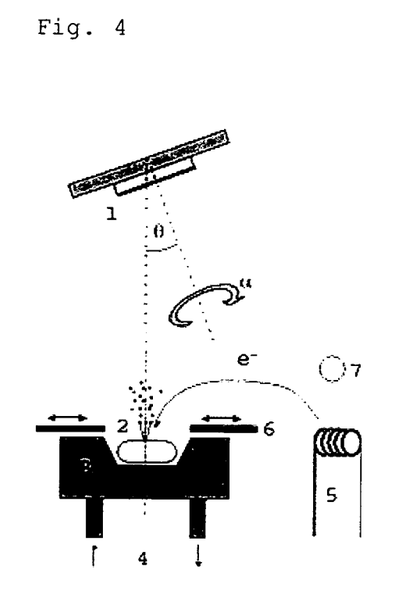
FIG. 4: Diagram of the modified evaporation system: 1) sample holder, 2) evaporation source, 3) crucible, 4) water cooling system,
5) electron beam source, 6) shutter, 7) magnetic field. θ is the evaporation angle and α is the rotation angle of the sample.

Metal deposition is carried out by evaporation using an e-beam evaporator. The evaporation system is modified to ensure control over the evaporation angle (è) and the sample rotation at the same time (FIG. 4).

4. Preparation of Nanostructures with Different Morphology

Figure 5:
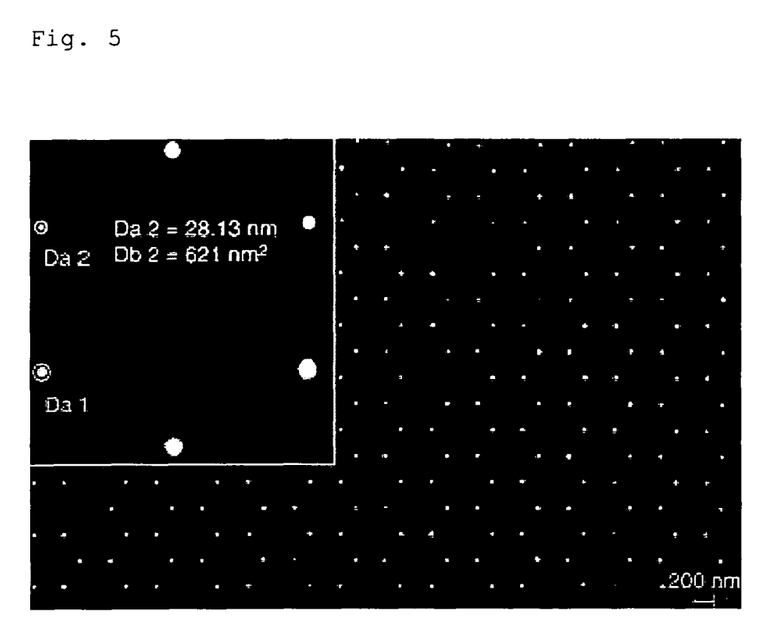
FIG. 5: Ordered spherical Co nanoparticles evaporated through an annealed 540-nm PS latex mask. The diameter of a single particle is approximately 30 nm.

An annealed mask with 30-nm apertures (FIG. 3) is used for the fabrication of Co magnetic nanoparticles or Au nanoparticles in a honeycomb lattice. A layer of Co or Au is evaporated (10 nm at 0.01 nms$^{-1}$) with the sample placed perpendicular to the evaporation beam. The result for Co particles is presented in FIG. 5. The size of the Co nanodot particles varies in a small regime and some of them are missing. These differences are all over the sample and arise during the annealing process, most probably because of the small differences (CV=2.4%) in PS sphere diameters.

Figure 6:
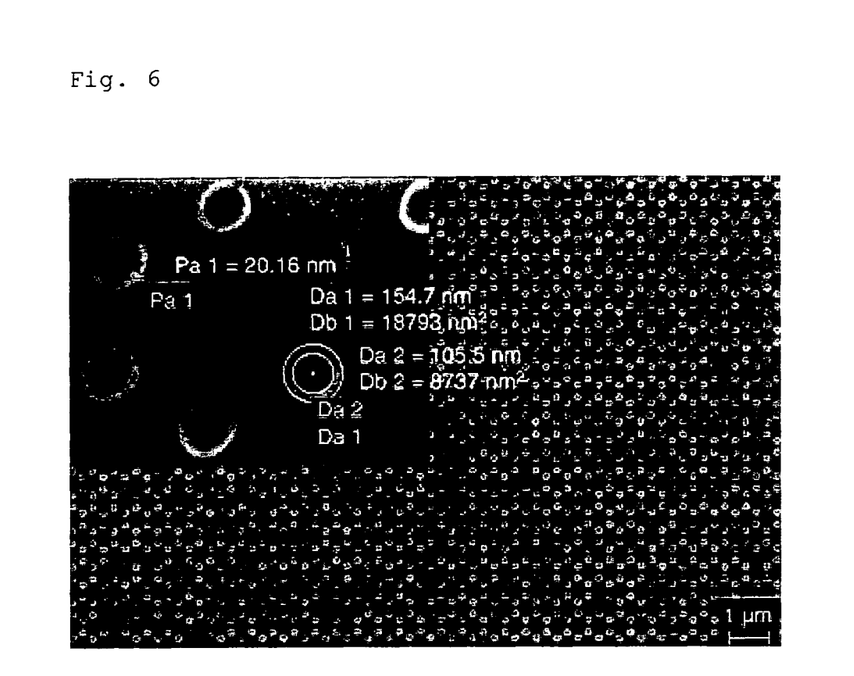
FIG. 6: SEM picture of ordered Fe nanorings evaporated through an annealed 540-nm PS latex mask.
The outer diameter of the single ring is 150 nm and the width of the ring is 20-30 nm.

We used similar masks for nanoring fabrication. In this experiment Fe was deposited (100 nm) through the annealed template from FIG. 3 at the evaporation angle □=258, and the sample was rotated during deposition. The rings had uniform outer (~150 nm) and inner (~100 nm) diameters (inset of FIG. 6), which could be controlled by altering the evaporation angle. The thickness of the rings in FIG. 6 is about 7 nm and can also be controlled by altering the aperture size of the nanosphere mask and the amount of deposited metal. In a previous paper, we discussed the relationship between the evaporation angle and the amount of deposited metal. Recently there have been many attempts to fabricate nanorings.[10,11] However, our method combines a very good control of the dimensions of the structures and fabrication materials with the reproducibility and simplicity of the preparation process.

[10] F. Yan, W. A. Goedel, Nano Lett. 2004, 4, 1193.
[11] J. McLellan, M. Geissler, Y. Xia, J. Am. Chem. Soc. 2004, 126, 10830.

EXAMPLE 2

We used the following strategy to specifically bind monoclonal IgG to Au nanoislands that were assembled on transparent or non-transparent substrates.

A 20 mM solution of succinimidyl 6-[3'-(2-pyridyldithio)-propionamido] hexanoate, (a SPDP reagent) [12] in DMSO (dimethylsulfoxide) or ethanol was incubated with our periodic arrays of nanostructures in the presence of 150 mM DTT (dithiothreitol) for 30 minutes. This procedure allows covalent linkage of thiol to Au nanoislands.

[12] N-succinimidyl 3-(2-pyridyldithio) propionate (SPDP reagents) are a unique group of amine- and sulfhydryl-reactive heterobifunctional cross-linkers. Whether they are used to form amine-to-amine or amine-to-sulfhydryl cross-links among molecules, the SPDP reagents produce disulfide-containing linkages that may be cleaved later with reducing agents such as dithiothreitol (DTT). The amine-reactive portion of SPDP reagents is the N-hydroxysuccinimide (NHS) ester. Reactions are most commonly performed in phosphate, carbonate/bicarbonate, or borate buffers at pH 7-8. Other buffers may be used provided they do not contain primary amines (or thiols or disulfide reducing reagent). The rate of reaction and degradation by hydrolysis increases with increasing pH; for example, the half-life of the NHS ester is several hours at pH 7 and less than 10 minutes at pH 9. NHS-ester reagents like SPDP and LC-SPDP have limited aqueous solubility and must be dissolved in organic solvent before adding them to a reaction mixture. Sulfo-NHS-ester reagents like Sulfo-LCSPDP are water-soluble and may be added directly to aqueous reaction mixtures.

The sulfhydryl reactive portion of SPDP reagents is the 2-pyridyldithio group, which reacts optimally with sulfhydryls between pH 7 and 8. The reaction results in displacement of a pyridine-2-thione group, the concentration of which may be determined by measuring the absorbance at 343 nm. Reaction buffers must be free of thiols and disulfide reducing agents until quenching or reduction of the 2-pyridyl disulfide is desired. Two basic strategies may be used to form cleavable cross-links between proteins with SPDP reagents, depending whether one or neither protein already possesses sulfhydryl groups (—SH) in addition to primary amines. Both conjugation methods result in cross-links that contain a disulfide bond in the spacer arm, which may be cleaved by reduction with dithiothreitol (DTT) or other reducing agent. In most cases, cross-links created using SPDP reagents can be cleaved with 25 mM DTT at pH 4.5 without reducing native protein disulfide bonds. However, when preservation of native disulfide bonds is not a concern, cleavage with DTT may be performed most efficiently at pH 7-9. Cross-linking experiments with SPDP reagents are not limited to those involving proteins. Any of a variety of molecules with primary amines (—NH2) and sulfhydryl groups may be modified or cross-linked using an SPDP reagent.

Figure 8:
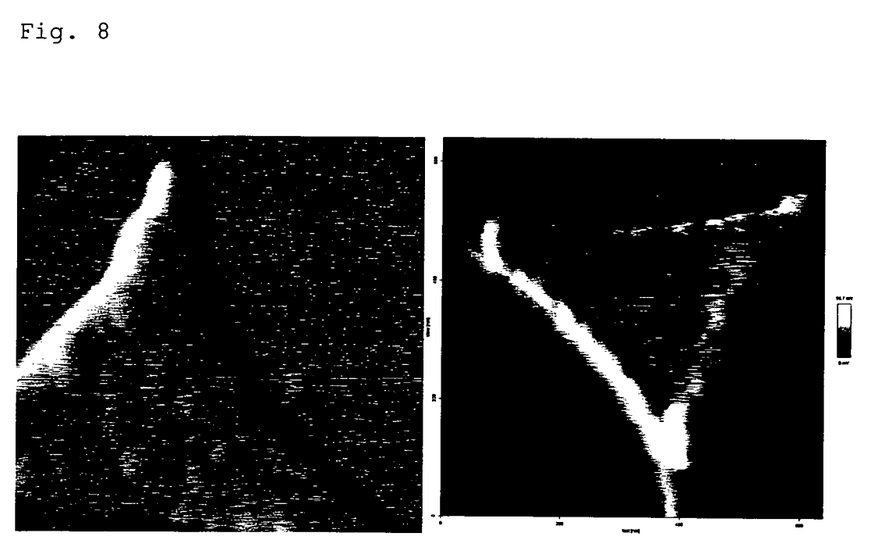
FIG. 8: IgG molecules covalently tethered to Au nanoislands through SPDP linker. The diameter of a single dot is 12 nm, corresponding to the average molecular weight of IgG (150 kD).

After cleaning the arrays with buffer (PBS-EDTA) bioorganic interactive material at concentrations from 0.5 to 2 mg/ml was incubated with the array for 1 h or over night. We revealed coatings as shown in FIG. 8 for the case that monoclonal IgG at a concentration of 1 mg/ml was used. The dimension of a single dot spot on gold is 12 nm, corresponding to the average molecular weight of a single IgG molecule of 150 kD.

Two examples how the "Diagnostic-Nanosensor" for in vitro use is applied:

1) Safe Production, Labelling And Transfusion Of Blood Components

Blood components are transfused in patients under special guidelines to insure safety of the recipient. These guidelines include determination of the blood type (basically AB0 and Rhesus type) of blood products and recipient. In addition, virus contaminations of blood products need to be excluded by specific measurements. Furthermore, blood components are labelled during storage in containers or bags showing the blood type and identification for "look back" procedures. The "Diagnostic-Nanosensor" according to the invention is functionalized with the appropriate bio-organic interactive material that enables the determination of the various human blood types or potential contaminating viruses (HIV, hepatitis B, hepatitis C). If the appropriate bio-organic interactive material is conjugated to self-luminescent nanoparticles, the interaction with the correspondent analyte reduces or obliterates luminescence that could easily detected by eye. The "Diagnostic-Nanosensor" according to the invention assembled in this way could be incorporated into the line through that blood is collected during blood donation, included into the bags that are used for blood component storage, or as "dipping" device to determine blood type of the recipient in small amount of blood obtained from the recipient. In any of these cases, blood type or contaminating viruses could be determined without additional equipment.

2) Determining the Homeostasis of Patients by Quantitative Measuring of Serum Components The quantitative measurement of serum components is frequently used to determine e.g. the coagulation or glucose homeostasis of a patient. The "Diagnostic-Nanosensor" according to the invention is functionalized with the appropriate bio-organic interactive material that enables the determination of the various components of the coagulation system or of glucose. Binding of a given component of the coagulation system or glucose to the functionalized nanostructured array change the plasmon resonance frequencies on the nanostructured surface of the "Diagnostic-Nanosensor" according to the invention and thus enables quantitative measurement of the component of interest. This measurement could be performed in a regular spectral-photometer or a hand held photometer that operates on batteries for "on-scene" use.

The invention claimed is:
1. A method for producing a Diagnostic-Nanosensor having a carrier and two-dimensioned arched metallic nanostructures with detection-molecules, the method comprising:

assembling said Diagnostic-Nanosensor on a spring wire or stent to form a molecular or cell select catheter configured for obtaining molecular or cellular components directly from intravenous blood circulation;

configuring said Diagnostic-Nanosensor to be applied through a hollow needle or through a venous line into a human blood vessel so that, when in use, the Diagnostic-Nanosensor can be retracted with attached cells and/or molecules for processing after an incubation time;

patterning the metallic nanostructures as periodic, surface-confined nanotriangles forming nanopatterned islands disposed in a hexagonal array, characterized by surface-confined rod-shaped horizontal nano-morphologies obtained by a sintering process of the surface-confined nanotriangles, wherein the nanopatterned islands are obtained by nanosphere lithography (NSL) with an annealing step of a polystyrene mask; and linking bio-organic interactive material to the nanostructures indirectly through linker technology.

2. The method according to claim 1, comprising:
arranging a monodisperse array of nanoislands so that the array has a tunable geometry.

3. The method according to claim 1, comprising:
linking the bio-organic interactive material to the nanostructures such that the binding of a target substance to the bio-organic interactive material induces a collective interaction with the surface electron (plasmon resonance).

4. The method according to claim 1, comprising:
linking the bio-organic interactive material to the nanostructures such that the binding of a target substance to the bio-organic interactive material creates an exiton interaction for detection by measuring luminescence or fluorescence.

5. The method according to claim 1, comprising:
linking the bio-organic interactive material to the nanostructures such that the binding of a target substance to the bio-organic interactive material can be measured by the interaction between ferro-and superparamagnetic materials.

6. The method according to claim 1, comprising:
linking the bio-organic interactive material to the nanostructures such that every metallic or non-metallic nanoisland acts as an individual sensor.

7. The method according to claim 3, comprising:
detecting and quantitatively measuring the assembly of target substances to individual nanoislands.

8. The method of claim 4, comprising:
detecting and quantitatively measuring the assembly of target substances to individual nanoislands.

9. The method of claim 5, comprising:
detecting and quantitatively measuring the assembly of target substances to individual nanoislands.

10. The method of claim 1, comprising:
selecting the metallic nanostructures from the group consisting of nanopatterned metal, semiconductors and magnetic-islands;

depositing the nanostructures on planar or non-planar, transparent or non-transparent surfaces; and depositing the bio-organic interactive material on the nanostructures to form a sandwich device for interacting with organic or inorganic targets.

11. The method of claim 1, comprising:
assembling the nanopatterned islands into a nanostructured periodic array of metallic nanoislands selected from the group consisting of nano-needles, wires, tubes, rings, and spheres.

12. The method of claim 10, comprising:
selecting the planar or non-planar, transparent or non-transparent surfaces from the group consisting of stainless steel; glass; silicon; and biocompatible polymers that are transparent or non-transparent and conductive or non-conductive; and selecting the metallic nanostructures from the group consisting of noble metals, semiconductors, Cobalt, and Nickel.

13. The method of claim 1, comprising:
selecting the bio-organic interactive material from the group consisting of antibodies, parts of antibodies, peptides, oligomers made of nucleic acids, and receptor structured organic or inorganic compounds that specifically interact with targets; and wherein the annealing step decreases the apertures in the polystyrene mask to 30 nm.

14. The method of claim 8, comprising:
selecting the metallic nanostructures from the group consisting of nanopatterned metal, semiconductors and magnetic-islands;

depositing the nanostructures on planar or non-planar, transparent or non-transparent surfaces; and depositing the bio-organic interactive material on the nanostructures to form a sandwich device for interacting with organic or inorganic targets.

15. The method of claim 1, wherein the linker technology is selected from the group consisting of streptavidin and N-Succinimidyl 3-(2-pyridyldithio)-propionate.

16. The method of claim 1, wherein the linking comprises:
incubating said nanostructures with an SPDP reagent; and
incubating said nanostructures linked to an SPDP reagent with bio-organic interactive material.

17. The method of claim 1, wherein the linking comprises:
incubating said nanostructures with streptavidin;
incubating said bio-organic interactive material with biotin; and
incubating said nanostructures linked to streptavidin with said bio-organic interactive material linked to biotin.

18. The method of claim 16, wherein said SPDP reagent is SPDP.

19. The method of claim 16, wherein said SPDP reagent is LC-SPDP.

20. The method of claim 16, wherein said SPDP reagent is Sulfo-LC-SPDP.

* * * * *